United States Patent

Andreas et al.

[11] Patent Number: 5,308,902
[45] Date of Patent: May 3, 1994

[54] BIPHOSPHITES

[75] Inventors: Holger Andreas, Bensheim/Auerbach, Fed. Rep. of Germany; Alfred Renner, Muntelier, Switzerland; Horst Zinke, Reichelsheim/Odw., Fed. Rep. of Germany

[73] Assignee: Ciba-Geigy Corporation, Ardsley, N.Y.

[21] Appl. No.: 882,993

[22] Filed: May 14, 1992

[30] Foreign Application Priority Data

May 16, 1991 [CH] Switzerland ............ 1462/91

[51] Int. Cl.$^5$ .................... C08K 5/52; C07F 9/02
[52] U.S. Cl. .................... 524/128; 524/120; 524/92; 524/101; 558/74; 558/77; 558/85
[58] Field of Search ............ 558/74, 77, 85; 524/120, 128

[56] References Cited

U.S. PATENT DOCUMENTS

| | | | |
|---|---|---|---|
| 3,039,993 | 6/1962 | Friedman | 524/120 |
| 3,310,609 | 3/1967 | Baranauckas et al. | 558/74 |
| 3,326,939 | 6/1967 | Guttag | 549/222 |
| 3,412,051 | 11/1968 | Baranauckas et al. | 521/170 |
| 3,737,485 | 6/1973 | Hechenbleikner | 558/74 |
| 4,206,111 | 6/1980 | Valdiserri et al. | 524/91 |

FOREIGN PATENT DOCUMENTS 1237312  3/1967  Fed. Rep. of Germany.
4021962  1/1992  Fed. Rep. of Germany.

OTHER PUBLICATIONS

Taschenbuch der Kunststoff-Additive (1983) pp. 8-15, 20-23, 232-237.
Methoden Der Organischen Chemie (1964).
Organic Syntheses vol. 4 (1963).
C.A. vol. 116, 1992.
Plastics Additives Handbook 3rd Ed. 1990 pp. 41-53.
Plastics Additives Handbook 3rd Ed. 1990 pp. 300-303.

*Primary Examiner*—Paul R. Michl
*Assistant Examiner*—Tae H. Yoon
*Attorney, Agent, or Firm*—Luther A. R. Hall; Michele A. Kovaleski

[57] ABSTRACT

Biphosphites of formula I

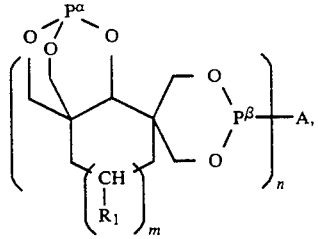

wherein
m is 0, 1 or 2,
n is 1 to 4 or 6,
$R_1$ is hydrogen or $C_1$-$C_4$alkyl and, if m=2, the radicals $R_1$ are identical or different, and A is the radical of an at least n-hydric alcohol or phenol, which radical is attached to the P atom or atoms through the alcoholic or phenolic O atom or atoms, obtainable by reacting a compound of formula II

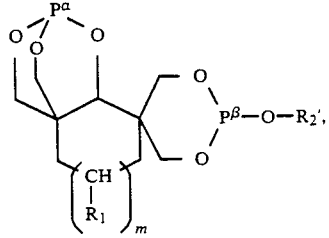

wherein m is 0, 1 or 2, $R_1$ is hydrogen or $C_1$-$C_4$alkyl and, if m=2, the radicals $R_1$ are identical or different and $R_2'$ is phenyl, $C_1$-$C_{12}$alkylphenyl or $C_1$-$C_4$alkyl, with a polyether polyol or polyether/ester polyol, the hydroxy functions of said polyether polyol or polyether/ester polyol being partially or completely esterified with the radical 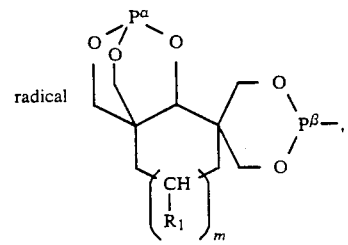

are suitable for use as stabilizers, especially processing stabilizers, for organic polymers, preferably PVC resins, high density polyethylene and propylene.

20 Claims, No Drawings

BIPHOSPHITES

The present invention relates to novel biphosphites, to compositions comprising said biphosphites, and to the use of the novel compounds as stabilisers for organic materials.

Organic phosphites and phosphonites are known in the art as co-stabilisers, secondary antioxidants and processing stabilisers. Thus a number of compounds of this type used in the art are described in the Taschenbuch der Kunstsoff-Additive (Manual of Plastics Additives) (Dr. R. Gächter, Dr. H. Müller, 2nd edition, 1983, pp. 232-236, 9-14 and 22; Carl Hanser Verlag, Munich, Vienna).

Spiro-bound biphosphites which are used as stabilisers for polyolefines are disclosed in DE-B-1 237 312 and U.S. Pat. No. 4,206,111. Phosphites prepared from 3,3,5,5-tetrakis(hydroxymethyl)-4-hydroxytetrahydropyran are disclosed in U.S. Pat. No. 3,326,939. This patent specification teaches the use of the phosphites as stabilisers for PVC resins, polypropylenes and other polymers, as flame-proofing additives and as lubricant oil additives.

It has now been found that biphosphites of formula I below are surprisingly good stabilisers for organic material, especially processing stabilisers for synthetic polymers.

Specifically, the invention relates to compounds of formula I

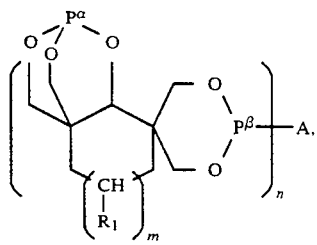

wherein
m is 0, 1 or 2,
n is 1 to 6,
$R_1$ is hydrogen or $C_1$-$C_4$alkyl and, if m=2, the radicals $R_1$ are identical or different, and A is the radical of an at least n-hydric alcohol or phenol, which radical is attached to the P atom or atoms through the alcoholic or phenolic O atom or atoms.

$R_1$ defined as $C_1$-$C_4$alkyl is methyl, ethyl, propyl, isopropyl, n-butyl, isobutyl or tert-butyl, preferably methyl. $R_1$ is preferably hydrogen.

The expression "at least n-hydric alcohol or at least n-hydric phenol" means that the alcohol or phenol may contain free OH functions in addition to the OH groups which are esterified with the phosphorus atom.

Particularly interesting compounds of formula I are those wherein A, if n=1, is —$OR_2$, wherein $R_2$ is $C_1$-$C_{24}$alkyl, unsubstituted or substituted by $C_5$-$C_{12}$cycloalkyl, morpholino, piperidino, piperazino, $C_6$-$C_{16}$alkylcycloalkyl, tetrahydrofuryl, phenyl, phenoxy and/or —$NR_3R_4$; $C_2$-$C_{24}$alkyl which is interrupted by one or more —O—, —S— and/or —$NR_5$ units; unsubstituted or $C_1$-$C_6$alkyl-substituted $C_5$-$C_{12}$cycloalkyl; phenyl, naphthyl or biphenyl, each unsubstituted or substituted by $C_1$-$C_{18}$alkyl, phenyl, phenyl-$C_1$-$C_4$alkyl, cyclopentyl, cyclohexyl and/or $C_2$-$C_4$alkenyl; or unsubstituted or $C_1$-$C_4$alkoxy-substituted phenyl-$C_1$-$C_4$alkyl, $R_3$ and $R_4$ are each independently of the other hydrogen, $C_1$-$C_6$alkyl, phenyl or ($C_1$-$C_4$alkyl)phenyl, $R_5$ is hydrogen, $C_1$-$C_6$alkyl or phenyl, A, if n=2, is a radical —O—Y—O—, wherein Y is $C_2$-$C_{20}$alkylene, $C_2$-$C_{20}$alkenylene or $C_3$-$C_4$alkynylene, each unsubstituted or substituted by $R_6$ and/or $R_7$, $C_2$-$C_{20}$alkylene which is interrupted by O-atoms, $C_5$-$C_6$cycloalkylene, $C_7$-$C_{12}$alkylenecycloalkylenealkylene, phenylene, naphthylene, 3,4-tetrahydrofurylene,

or is a radical —X—B—X—, X is unsubstituted or $C_1$-$C_4$alkyl-substituted $C_1$-$C_{20}$alkylene, $C_5$-$C_6$cycloalkylene, phenylene or phenylene which is substituted by $C_1$-$C_4$alkyl or $C_2$-$C_4$alkenyl, or is a radical

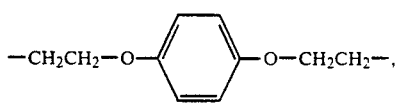

B is a direct bond, —$CR_6R_7$—, —S—, —$SO_2$— or —$R_5$—, $R_6$ is hydrogen or $C_1$-$C_4$alkyl, $R_7$ is hydrogen, $C_1$-$C_4$alkyl or $C_2$-$C_{12}$alkoxycarbonyl-$C_1$-$C_4$alkyl, or

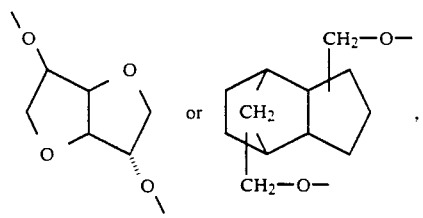

A is
A, if n=3, is

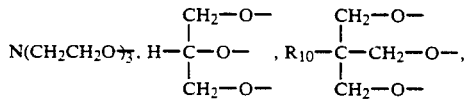

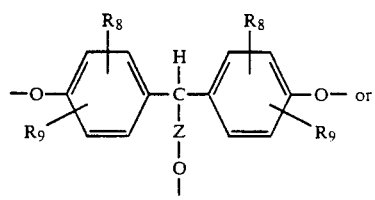

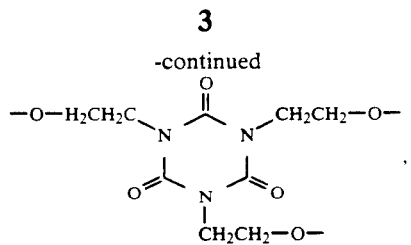

$R_8$ and $R_9$ are each independently of the other hydrogen or $C_1$-$C_4$alkyl, $R_{10}$ is $C_1$-$C_{24}$alkyl and Z is phenylene-($C_1$-$C_4$alkylene) which is substituted by 1 to 4 $C_1$-$C_4$alkyl groups, A, if n=4, is

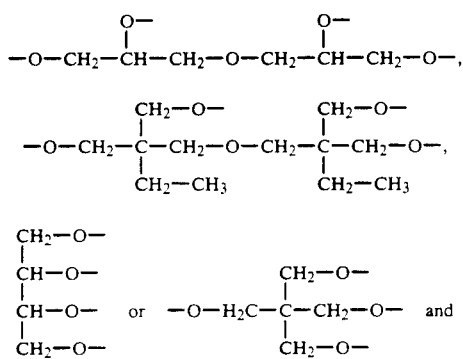

A, if n=5 or 6, is

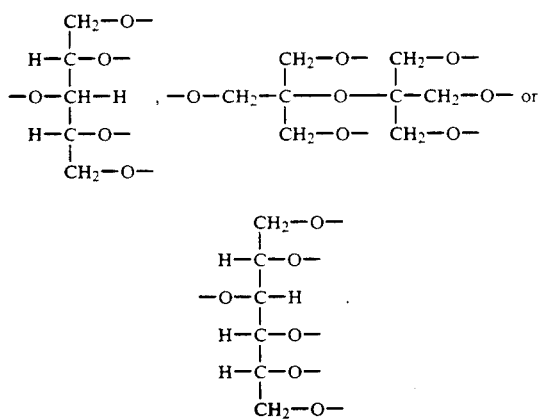

$R_1$ to $R_{10}$ defined as alkyl are branched or unbranched radicals. The numerical range indicated in connection with the symbol C denotes the number of possible carbon atoms.

$R_2$ and $R_{10}$ defined as $C_1$-$C_{24}$ alkyl may typically be methyl, ethyl, propyl, isopropyl, n-butyl, isobutyl, tert-butyl, pentyl, isopentyl, hexyl, heptyl, octyl, 2-ethylhexyl, nonyl, decyl, isodecyl, undecyl, dodecyl, tridecyl, tetradecyl, pentadecyl, hexadecyl, heptadecyl, octadecyl, 2-ethylbutyl, isoamyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl, nonadecyl, icosyl, henicosyl, docosyl, tricosyl or tetracosyl. The alkyl radicals of 4 to 20 carbon atoms are preferred, and those of 8 to 15 carbon atoms are particularly preferred.

Where $R_2$ is alkyl interrupted by —O—, —S— or —$R_5$ units, then the structural units present in the chain will typically be —$CH_2$—$CH_2$—O—, —$CH_2$—$CH_2$—S— or —$CH_2$—$CH_2$—$NR_5$—. One or more of the groups —$NR_5$—, —O— and —S— may be present in the chain. —$CH_2$—$CH_2$—O units are preferred.

$R_2$ defined as $C_5$—$C_{12}$cycloalkyl may be cyclopentyl, cyclohexyl, cycloheptyl, cyclooctyl, cyclodecyl and cyclododecyl. Cyclopentyl, cyclohexyl and cycloheptyl are preferred, and cyclohexyl is especially preferred.

Cycloalkyl may also be an alkyl radical which consists of a plurality of cyclic systems, conveniently bi- or tricyclic systems, typically tricyclodecyl or bicycloheptyl.

$C_1$-$C_4$Alkyl-substituted cycloalkyl may be mono- to trisubstituted, preferably monosubstituted. Possible substituents are methyl, ethyl-, propyl or butyl groups, as well as isomers of propyl and butyl.

$R_2$ defined as $C_1$-$C_{18}$alkyl-substituted phenyl may be: methylphenyl, dimethylphenyl, trimethylphenyl, ethylphenyl, diethylphenyl, isopropylphenyl, tert-butylphenyl, di-tert-butylphenyl, methyl-di-tert-butylphenyl, pentylphenyl, octylphenyl, nonylphenyl, dodecylphenyl or octadecylphenyl. The number of alkyl groups is preferably 1-3, conveniently 1 or 2. The total number of carbon atoms of all alkyl substituents is preferably 1 to 12.

$R_2$ defined as phenyl-$C_1$-$C_4$alkyl-substituted phenyl may be benzylphenyl, phenylethylphenyl, 3-phenylpropylphenyl, α-methlbenzylphenyl or α,α-dimethylbenzylphenyl.

$R_2$ defined as naphthyl is 1- or 2-naphthyl.

$R_2$ defined as phenyl-$C_1$-$C_4$alkyl may be benzyl, phenylethyl, 3-phenylpropyl, α-methylbenzyl or α,α-dimethylbenzyl, preferably benzyl.

$R_3$-$R_5$ defined as $C_1$-$C_6$alkyl may be methyl, ethyl, propyl, isopropyl, n-butyl, isobutyl, tert-butyl, pentyl or hexyl, preferably methyl.

$R_3$ and $R_4$ defined as ($C_1$-$C_4$alkyl)phenyl may be phenyl which is substituted by 1 to 4, preferably 1 to 3 or 1 or 2 alkyl groups, most preferably by one alkyl group, and are typically tolyl, xylyl, mesityl, tert-butylphenyl, ethylphenyl or isopropylphenyl, preferably tolyl.

$R_6$-$R_9$ defined as $C_1$-$C_4$alkyl may be methyl, ethyl propyl, isopropyl, n-butyl, isobutyl or tert-butyl, preferably methyl or tert-butyl.

$R_6$ and $R_7$ are preferably hydrogen or methyl.

$R_7$ as $C_2$-$C_{12}$alkoxycarbonyl-$C_1$-$C_4$alkyl may be methoxycarbonylmethyl, methoxycarbonylethyl, methoxycarbonylpropyl, ethoxycarbonylbutyl, ethoxycarbonylmethyl, ethoxycarbonylethyl, ethoxycarbonylpropyl, ethoxycarbonylbutyl, butoxycarbonylmethyl, butoxycarbonylethyl, decyloxycarbonylmethyl, decyloxycarbonylethyl, dodecyloxycarbonylethyl or dodecyloxycarbonylmethyl, preferably alkoxycarbonylethyl. X and Y as $C_1$-$C_{20}$alkylene may be methylene, ethylene, propylene, butylene, pentylene, hexylene, heptylene, octylene, nonylene, decylene, dodecylene, tridecylene, tetradecylene, pentadecylene, hexadecylene, heptadecylene, octadecylene, nonadecylene or isosylene. Y as $R_6$- and/or $R_7$-substituted alkylene is preferably $C_1$-$C_4$alkyl-substituted, preferably methyl-substituted, alkylene. X as $C_1$-$C_4$alkyl-substituted alkylene is methyl- or tert-butyl-substituted, preferably methyl-substituted, alkylene.

Where Y is $C_2$-$C_{20}$alkylene which is interrupted by O atoms, then the structural units present in the chain may be $-CH_2-CH_2-O-$. The chain may be interrupted by one or more O atoms.

Y defined as $C_2-C_{20}$alkenylene may be ethenylene, propenylene butenylene, pentenylene, hexenylene, heptenylene, octenylene, nonenylene, decenylene, dodecenylene, tridecenylene, tetradecenylene, pentadecenylene, hexadecenylene, heptadecenylene, octadencenylene, nonadecenylene or icosenylene. The appropriate alkenylene units may be mono- or polyunsaturated, preferably mono- to tri-unsaturated, most preferably mono-unsaturated.

Y as $C_3-C_4$alkynylene is propynylene or butynylene.

X and Y as $C_5-C_6$cycloalkylene are cyclopentylene or cyclohexylene.

Y as $C_7-C_{12}$alkylenecycloalkylene-alkylene may be an alkylene radical which is interrupted by cycloalkylene units. The cycloalkylene units are preferably cyclopentylene and cyclohexylene, preferably cyclohexylene. They may therefore typically be alternating ethylene and cyclohexylene groups, or alternating methylene and cyclohexylene groups, preferably methylenecyclohexylenemethylene. The term "cycloalkylene" can also mean an alkylene radical which consists of a plurality of cyclic systems, for example bi- or tricyclic systems, typically tricyclodecylene or bicycloheptanylene, preferably tricyclodecylene.

X as $C_1-C_4$alkyl-substituted phenylene may be phenylene which is substituted by 1 to 4, preferably 1 to 3 or 1 or 2, alkyl groups, most preferably by one alkyl group, and is typically toylene, xylylene, mesitylene, tert-butylphenylene, ethylphenylene or isopropylphenylene, preferably tolylene.

If Z is phenylene-($C_1-C_4$alkylene) which is substituted by 1 to 4 $C_1-C_4$alkyl groups; said alkyl groups may be substituents of the phenylene ring and/or the alkylene unit. Suitable $C_1-C_4$alkyl substituents may methyl, ethyl, propyl, isopropyl, butyl, isobutyl or tert-butyl, preferably methyl and tert-butyl. The alkylene unit consists of 1 to 4, preferably 2 or 3, carbon atoms.

$C_2-C_4$Alkenyl substituents may be vinyl, allyl, 2-methylprop-1-en-1yl, but-1-en-1yl, but-2en-2yl, but-2en-1yl, but-3-en-1yl or but-3-en-2-yl, preferably vinyl or allyl.

Particularly interesting compounds of formula I are those wherein m is 1.

Preferred compounds of formula I are also those wherein n is 1.

Interesting compounds of formula I are those wherein $R_2$ is unsubstituted or phenyl-substituted $C_1-C_{24}$alkyl, $C_2-C_{16}$alkyl which may be interrupted by one or more $-O-$, $-S-$ or $-H$ units, unsubstituted or $C_1-C_4$alkyl-substituted $C_5-C_{10}$cycloalkyl, unsubstituted phenyl or phenyl which is substituted by $C_1-C_{18}$alkyl, phenyl or phenyl-$C_1-C_4$alkyl, or naphthyl or phenyl-$C_1-C_4$alkyl.

Further preferred compounds of formula I are those wherein $R_2$ is unsubstituted or phenyl-substituted $C_4-C_{20}$alkyl, $C_4-C_{12}$alkyl which may be interrupted by one or more $-O-$, $-S-$ or $-H$ units, unsubstituted or $C_1-C_4$alkyl-substituted $C_6-C_{10}$cycloalkyl, unsubstituted phenyl or phenyl which is substituted by $C_1-C_{12}$alkyl, phenyl or phenyl-$C_1-C_4$alkyl, or $R_2$ is phenyl-$C_1-C_4$alkyl.

Other compounds of formula I which merit interest are those wherein n>1 ist, A is a radical $-O-Y-O-$, wherein Y is unsubstituted $C_2-C_{20}$alkylene or $C_2-C_{20}$alkylene which is substituted by $R_6$ and/or $R_7$, $C_2-C_{20}$alkylene which is interrupted by O atoms, $C_7-C_{12}$alkylenecycloalkylene-alkylene, phenylene, naphthylene or a radical $-X-B-X-$, X is unsubstituted or $C_1-C_4$alkyl-substituted $C_1-C_{20}$alkylene, phenylene or phenylene which is substituted by $C_1-C_4$alkyl or $C_2-C_4$alkenyl, B is a direct bond, $-NR_5-$, $-S-$ or $-CR_6R_7-$, or A is

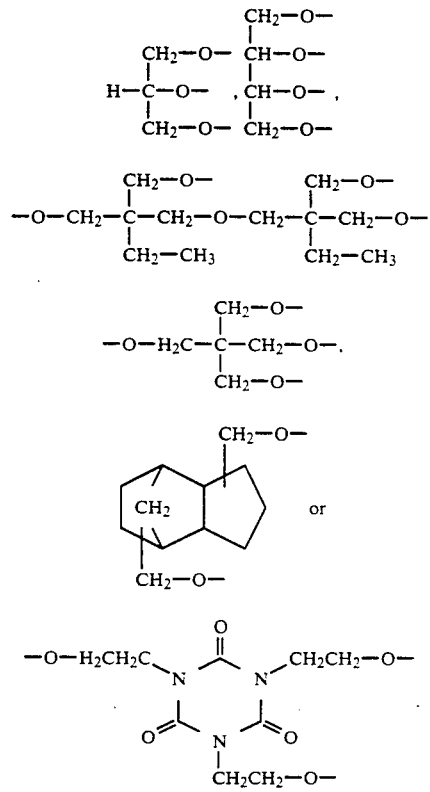

Further preferred compounds of formula I are those wherein A is the radical of an n-hydric linear or cyclic sugar in which not all OH groups of said sugar are esterified with a biphosphite radical.

Suitable sugars are typically sorbitol, anhydrosorbitol, dianhydridosorbitol, erythritol, xylitol or inositol.

The invention also relates to compounds which are obtainable by reacting compounds of formula II

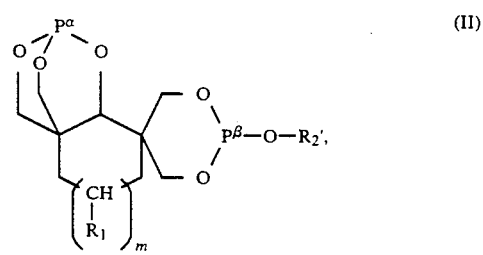 (II)

wherein m is 0, 1 or 2, $R_1$ is hydrogen or $C_1-C_4$alkyl and, if m=2, the radicals $R_1$ are identical or different and $R_2'$ is phenyl, $C_1-C_{12}$alkylphenyl or $C_1-C_4$alkyl, with a polyether polyol or polyether/ester polyol, the hydroxy functions of said polyether polyol or polyether/ester polyol being partially or completely esterified with the radical

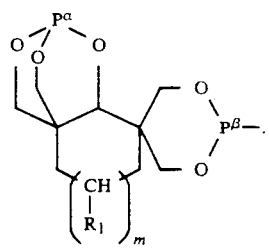

Polyether polyols are described, inter alia, in Ullmanns Encyclopädie der technischen Chemie (Ullmann's E.cyclopedia of Industrial Chemistry), 4th ed. Vol. 19, Verlag Chemie GmbH, Weinheim 1980, pp. 31-38 and pp. 304, 305, and can be obtained conveniently by reaction of a starter with alkylene oxides, typically with ethylene, propylene or butylene oxides, or tetrahydrofuran. By polyether/ester polyols are meant those branched polyols which contain ether as well as ester groupings, for example Desmophen® 1140, 1145, 1150 and 1155 sold by BAYER AG. It is preferred to use trifunctional branched polyethers based on propylene oxide. The OH numbers of the polyether polyols or polyether/ester polyols are typically in the range from 10–1000, conveniently from 20–1000, preferably from 30–800, most preferably from 30–700. The preparation of further suitable polyether polyols is described in DE-A-40 21 962.

Preferred compounds are those in which the polyether polyol or polyether/ester polyol is a polyol based on propylene oxide.

Particularly preferred compounds are those wherein m is 1 and $R_1$ is hydrogen.

The preparation of the novel compounds is carried out in accordance with the standard methods for preparing triphosphites. These standard methods are published, inter alia, in Houben-Weyl, Methoden der organischen Chemie XII/2, 73–78 (1964). Typically the compounds are prepared from triphenyl phosphite by transesterification with tetramethylcyclohexanol and suitable alcohols, alkyl phenols, diols or polyols or polyether polyols or polyether/ester polyols.

The compounds can thus conveniently be prepared in two steps:

(a) esterification of 2,2,6,6-tetramethylolcyclohexanol or analogous compounds and (b) 4ransesterification of the reaction product.

In the first step, 2,2,6,6-tetramethylolcyclohexanol or an analogous compound is reacted with a triarylphosphite or trialkylphosphite in the stoichiometric ratio of 1:2:

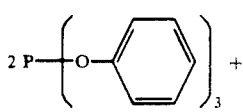

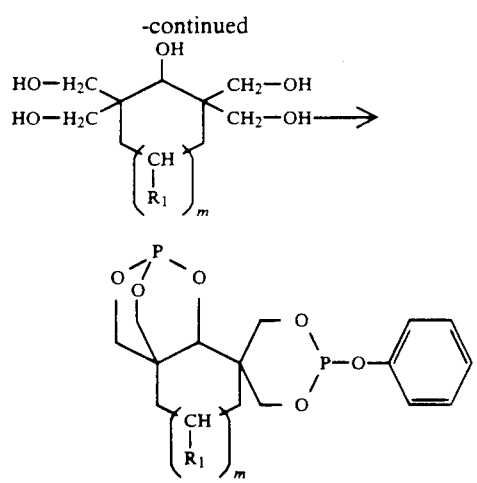

In the transesterification step, the phenyl group is replaced by another radical by reacting the reaction product with a suitable mono-, bi- or polyfunctional alcohol, alkyl phenol or polyether polyol or polyether/-ester polyol, with the elimination of phenol, to give the corresponding biphosphite (in the reaction with a trialkylphosphite, the transesterification step can be dispensed with):

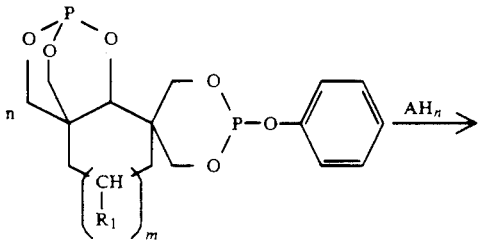

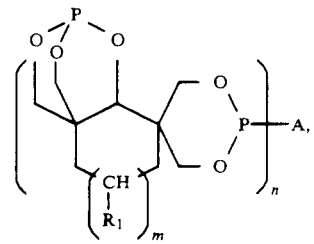

Both reaction steps are conveniently carried out in the presence of a base such as an alkali metal alcoholate, for example potassium or sodium methanolate, potassium or sodium ethanolate, sodium or potassium tert-butanolate or lithium amide. The reaction temperature may be in the range from 70°–160° C., preferably from 90°–120° C. The reaction times vary from 1 to 5, preferably 2 to 3, hours, depending on the temperature and specific reaction. If desired, the transesterification step can be carried out in an inert organic solvent, conveniently an aliphatic or aromatic hydrocarbon such as pentane, hexane, cyclohexane, benzene, toluene or xylene.

The starting materials for the preparation of the novel compounds are commonly known. Triphenylphosphite, for example, is sold by Ciba-Geigy under the registered trademark ®IRGAFOS TPP.

The synthesis of 2,2,6,6-tetramethylolcyclohexanol is set forth in Organic Syntheses, Vol. IV, 907-9 (Wiley &

Sons, Inc., New York, London). The compounds analogous to 2,2,6,6-tetramethylolcyclohexanol can be prepared by the same route from the corresponding cyclic ketones.

The following alcohols, alkyl phenols, polyols or polyether polyols or polyether/ester polyols may be used for the preparation of the novel biphosphites:

n-butanol, n-hexanol, n-octanol, 2-ethylhexanol, isobutyl alcohol, isoamyl alcohol, isooctyl alcohol, n-decanol, n-dodecyl alcohol, myristyl alcohol, stearyl alcohol, 2-butyloctan-1-ol, 2-hexyloctan-1-ol, cetyl alcohol, 2-butyldecan-1-ol, 2-hexyldodecan-1-ol, 2-octyldodecan-1-ol, n-icosan-1-ol, n-docosan-1-ol, 3,3-dimethylbutan-1-ol, pentadecan-1-ol, tridecan-1-ol, 2,6,8-trimethylnonan-4-ol, 4-methylpentan-2-ol, 2,6-dimethylheptan-4-ol, 3,4,5-trimethylheptan-1-ol, tetramethylnonan-1-ol, dimethylhexan-1-ol, 2,4-dimethylpentan-3-ol, 3-thiahexanol, ethyl triglycol, butyl glycol, butyl diglycol, butyl triglycol, ethyl thioethanol, ethylene glycol monoethyl ether, 1-morpholinopropan-2-ol, 3-dimethylaminopropan-1-ol, 2-[N,N-phenylmethyl]ethanolamine, 1-diethylaminobutan-2-ol, 3-phenyloxypropan-1-ol, methyl diglycol, 2-ethylbutan-1-ol, 2,3-dimethylbutan-1-ol, cyclohexanol, cyclododecanol, 8-hydroxytricyclo[5.2.1.0$^{2,6}$]decane, 3,3,5-trimethylcyclohexanol, 2-dibutylaminoethanol, 2-butylaminoethanol, 2-hexadecanol, heptan-4-ol, 3,3,5-trimethylhexan-1-ol, 2-[N,N-ethyl-o-methylphenyl]ethanolamine, ethylene glycol mono-n-butyl ether, cyclooctanol, 4-tert-butylcyclohexanol, 4-tert-amylcyclohexanol, 2-tert-butylcyclohexanol, 2-isopropyl-5-methylcyclohexanol, cyclopentanol, dimethyl isopropanolamine, tricyclodecyl carbinol, 1-cyclohexylethanol, cyclohexyl carbinol, 2-cyclohexylpropan-1-ol, tetrahydrofurfuryl alcohol, 4-tert-butylhydroxymethylcyclohexane, benzyl alcohol, phenylmethyl carbinol, 2-phenylpropan-2-ol, o-tolyl alcohol, 2-phenylethanol, 3-cyclohexylpropan-1-ol, 1,7,7-trimethylbicyclo[2.2.1]heptan-2-ol, 4-methoxybenzyl alcohol, 2-phenoxyethanol, 3,7-dimethyloctan-3-ol, methyl triglycol, polyethylene glycol monobutyl ether, 2-cyclohexylethanol, 2-methoxyethanol, m-cresol, benzylphenol, p-tert-octylphenol, nonylphenol, dodecylphenol, 2-tert-butyl-4-methylphenol, o-sec-butylphenol, isooctylphenol, 2,4,6-trimethylphenol, dinonylphenol, ethylphenol, mixture of 2,4(2,5)-dimethylphenol, p-tert-butylphenol, o-cyclohexylphenol, 2-cyclohexyl-4-methylphenol, p-cumylphenol, 2,4-di-tert-butylphenol, 2,4-di-tert-amylphenol, isopropylphenol, o-phenylphenol, p-phenylphenol, o-allylphenol, 2-tert-butyl-4-methylphenol, 2,4-dimethyl-6-ethylphenol, 2-isopropyl-5-methylphenol, 2-tert-butyl-5-methylphenol, 2-tert-butyl-4,5-dimethylphenol, 1-naphthol, 2-naphthol, 2,4-di-tert-butyl-5-methylphenol, p-tert-octyl-o-tert-butylphenol, 2-tert-butyl-4-dodecylphenol, 5-isopropyl-3-methylphenol, 3,5-di-tert-butylphenol, 3-pentadecylphenol, 1,4-butanediol, 1,5-pentanediol, 1,6-hexanediol, 3-methyl-1,5-pentanediol, 1,4-cyclohexanediol, 1,4-bis(hydroxymethyl)cyclohexane, 2,2'-bis[4-hydroxycyclohexyl]propane, 1,10-decanediol, propylene glycol, 1,12-dodecandiol, dipropylene glycol, 2,2'-bis[4-hydroxyphenyl]propane, 2,2'-bis[4-hydroxy-3-allylphenyl]propane, 3,4-dihydroxyfuran, -butyldiethanolamine, N,N-bis(hydroxyethyl)amine, 2,2,4-trimethyl-1,6-hexanediol, bis(hydroxyethyl)sulfone, 4,4'-dihydroxybiphenyl, diethylene glycol, triethylene glycol, tetraethylene glycol, polyethylene glycol 300, polyethylene glycol 400, bis[4-hydroxylphenyl]sulfide, bis[4-hydroxyphenyl]sulfone, bis(2-hydroxyethyl)sulfone, thiodiglycol, bis(hydroxymethyl)tricyclodecane, 2-methylpentane-2,4-diol, triisopropanolamine, bis(trimethylol)propane, tris(hydroxyethyl)isocyanurate, phenyldiethanolamine, diisopropanolamine, dianhydrosorbitol, erythritol, xylitol, inositol, triethanolamine, 2-methyl-2,4-pentanediol, 2,2-ethylbutyl-1,3-propanediol, 4,4-bis[4-hydroxyphenyl]valerianate, polyethylene glycol 200, polyethylene glycol 600, polypropylene glycol P 400, 1,5-dihydroxynaphthalene, 2,7-dihydroxynaphthalene, thiodipropylene glycol, anhydrosorbitol, pentaerythritol, dipentaerythritol, 1,1-bis[4'-hydroxy-5'-tert-butyl-2'-methylphenyl]butane, glycerol, 4,4'-thiobis[3-methyl-6-tert-butylphenol], 1,1,3-tris[2'-methyl-4'-hydroxy-5'-tert-butylphenyl]butane, Desmophen ® 550 U, Desmophen ® 1155 U (ex BAYER AG), Voranol ® CP 455, Voranol ® CP 755, Voranol ® CP 255 (ex DOW Chemical Corp.), Lupranol ® 3421 (ex BASF).

The compounds of formula I and the compounds obtainable as described above by transesterification with polyether polyols or polyether/ester polyols are admirably suitable for stabilising organic materials against light-induced, thermal and/or oxidative degradation. The compounds also have flame-retardant properties on account of the chemically bound phosphorus. The compounds have good stability to hydrolysis.

The invention also relates to compositions comprising an organic material which is susceptible to light-induced, thermal and/or oxidative degradation and at least one compound of formula I or a compound obtainable as described above by transesterification with polyether polyols or polyether/ester polyols, and to the use of compounds of formula I or of compounds obtainable as described above by transesterification with polyether polyols or polyether/ester polyols as stabilisers for organic materials against the types of degradation referred to above.

Exemplary of such materials are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/EVA, LDPE/EAA, LLDPE/EVA and LLDPE/EAA.

3a. Hydrocarbon resins (for example C$_5$-C$_9$), including hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, for example styrene|[ch-]butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example poly- vinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer; polyacetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or polybutadienes carrying terminal hydroxyl groups on the one hand and aliphatic or aromatic polyisocyanates on the other, as well as precursors thereof.

15. Polyamides and copolyamides which are derived from diamines and dicarboxylic acids and |[ch] or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins derived from substituted acrylic esters such as epoxy acrylates, urethane acrylates or polyester acrylates.

24. Alkyd resins, polyester resins or acrylate resins which are cross-linked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.

27. Mixtures (polyblends) of the aforementioned polymers, for example PP/EPDM, Polyamides 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fasts, oil and waxes, or oils, fats and waxes based on synthetic esters (e.g. phthalates, adipates, phosphates or trimellitates) and also the mixtures of synthetic esters with mineral oils in any weight ratios which are used as spinning compositions, as well as aqueous emulsions of such materials.

29. Aqueous emulsions of natural or synthetic rubber, for example natural latex or latices of carboxylated styrene/butadiene copolymers.

The organic materials to be protected are preferably natural, regenerated or, most preferably, synthetic organic materials. Especially preferred organic materials are thermoplastic polymers, more particularly polyolefins, typically polyvinyl chloride (PVC), polyethylene, preferably high density polyethylene (HDPE) and polypropylene (PP).

The novel compositions conveniently contain the compounds of formula I or the compounds obtainable as described above by transesterification with polyether polyols or polyether/ester polyols in amounts of 0.01 to 10, conveniently 0.05 to 5, preferably 0.05 to 3, but most preferably 0.1 to 2% by weight. The compositions may contain one or more compounds of formula I, and the amounts by weight refer to the total amount of these compounds. The basis for the calculation is the total weight of the organic material without the compounds of formula I.

The novel compounds can be incorporated into the materials by blending or applying the compounds and other optional additives by standard methods used in the art. If the materials are polymers, especially synthetic polymers, incorporation can be effected before or during shaping, or by applying the dissolved or dispersed compounds to the polymer and, if required, evaporating the solvent. If the materials are elastomers, these may also be stabilised as lattices. A further means of incorporating the novel compounds into polymers consists in adding them before, during or immediately after the polymerisation of the appropriate monomers or before crosslinking. The novel compounds can also be added in the pure form as well as in encapsulated form (e.g. in waxes, oils or polymers). If the novel compounds are incorporated before or during the polymerisation, then they can also act as regulators for the chain length of the polymers (chain 4%2minators).

The novel compounds or mixtures thereof can also be added to the plastics materials to be stabilised in the form of a masterbatch which contains these compounds conveniently in a concentration of 2.5 to 25% by weight.

The novel compounds can be incorporated by the following methods:

as emulsion or dispersion (e.g. to lattices or emulsion polymers)

as dry mix during the mixing of additional components or polymer blends by direct addition to the processing apparatus (e.g. extruder, internal mixer etc.)

as solution or melt.

Novel polymer compositions can be used in different form and processed to different products, typically to films, filaments, ribbons, mouldings, profiles, casting resins, laminates, or they are used as binders for paints and varnishes, as binders for making honeycomb structures, adhesives, such as structural adhesives for metals and plastics or putties.

As already mentioned, the materials to be protected are organic, preferably synthetic, polymers. It is especially useful to protect thermoplastic materials, preferably polyolefins. To be singled out for special mention in this connection is the excellent efficacy of the novel compounds, especially those of formula I, as processing stabilisers (heat stabilisers). To this end they are conveniently added before or during the processing of the polymer.

It is, however, also possible to protect other polymers (e.g. elastomers) against degradation, typically light-induced and/or thermal-oxidative degradation. Examples of elastomers will be found in the foregoing recitation of possible organic materials.

The suitable lubricants and hydraulic fluids are known to the skilled person and are described, for example, in Dieter Klamann "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974, or in "Ullmanns E.cyclopädie der technischen Chemie" (Ullmann's Encyclopedia of Industrial Chemistry), Vol. 13, pages 85–94 (Verlag Chemie, Weinheim, 1977).

The invention also relates to a process for protecting organic material against oxidative, thermal and/or actinic degradation, which comprises incorporating in or applying to said material compounds of formula I or compounds obtainable as described above by transesterification with polyether polyols or polyether/ester polyols as stabilisers.

In addition to comprising the novel compounds, the compositions of the invention, especially if they contain organic, preferably synthetic, polymers, may comprise further customary additives. Exemplary of such additives are:

1. Antioxidants 1.1.. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-di-nonyl-4-methylphenol, 2,4-dimethyl-6-(1'-methyl-undec-1'-yl)phenol, 2,4-dimethyl-6-(1'-methyl-heptadec-1'-yl)phenol, 2,4-dimethyl-6-(1'-methyl-tridec-1'-yl)phenol and mixtures thereof.

1.2. Alkylthiomethylphenols, for example 2,4-dioctylthiomethyl-6-tert-butylphenol, 2,4-di-octylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-Di-tert-butyl-4-methoxyphenol, 2,5-di-tert-butyl-hydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-ditert-butyl-4-hydroxyanisole, 3,5-di-tert-butyl-4-hydroxyphenylstearate, bis(3,5-di-tert-butyl-4-hydroxyphenyl)adipate.

1.4. Hydroxylated thiodiphenylethers, for example 2,2'-thiobis-(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis-(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis-(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-(4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl) dicyclopentadiene, bis[2-(3'-tert-butyl-2'-hydroxy-5'-methylbenzyl)-6-tertbutyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O-, N- and S-benzyl compounds, for example 3,5,3',5'-tetra(tert-butyl-4,4'-dihydroxydibenzyl) ether, octadecyl-4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.7. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis-(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazines, for example 2,4-bis[(octylmercapto-6-(3,5-di-tert-butyl-4-hydroxyanilino)]-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, di-octadecyl-5-tert-butyl-4-hydroxy-3-methylbenzylphosphonate, the calcium salt of monoethyl 3,5-di-tert-butyl-4-hydroxybenzylphosphonate.

1.11. Acylaminophenols, for example 4-hydroxylauryl anilide, 4-hydroxystearyl anilide, octyl -(3,5-di-tert-butyl-4-hydroxyphenyl)carbamate.

1.12. Esters of β-(3,5-di-tertbutyl-4-hydroxyphenyl)-propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.13. Esters of β-(5-tert-butyl-4-hydroxy-3-methylphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.14. Esters of β-(3,5-dicyclohexyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.-2]octane. 1.15. Esters of 3,5-di-tert-butyl-4-hydroxyphenylacetic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.-2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, ,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and light stabilisers 2.1.2-(2'-Hydroxyphenyl)benzotriazoles, for example the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octyloxy-, 3',5'-di-tert-amyl-or 3',5'-bis(α,α-dimethylbenzyl)- mixture of 5-chloro-3'-tert-butyl-5'-(2-octyloxycarbonylethyl)-and 5-chloro-3'-tert-butyl-5'-[2-(2-ethylhexyloxy)-carbonylethyl]-, 5-chloro-3'-tertbutyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)-carbonylethyl]-, 3'-dodecyl-5'-methyl- and 3'-tert-butyl-5'-(2-isooctyloxycarbonylethyl)-2'-hydroxyphenyl-2H-benzotriazol-2-yl, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R-CH$_2$CH$_2$-COO(CH$_2$)$_3$]$_2$, wherein R=3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative. 3,5-di-tert-butyl-4-hydroxybenzoic acid, hexadecyl 3,5-di-tert-butyl-4-hydroxybenzoate, octadecyl 3,5-di-tert-butyl-4-hydroxybenzoate, the 2-methyl-4,6-di-tert-butylphenyl ester of 3,5-di-tert-butyl-4-hydroxybenzoic acid.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1- or 1:2 complex, with or without additional ligands, as n-butylamine, triethanolamine or N-cyclohexyl-diethanolamine, nickel dibutyl dithiocarbamate, nickel salts of monoalkyl esters of 4-hydroxy-3,5-di-tert-butylbenzylphosphonic acid, as of methyl or ethyl esters, nickel complexes of ketoximes, as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, the bis(1,2,2,6,6-pentamethylpiperidyl) ester of n-butyl-3,5-di-tert-butyl-4-hydroxybenzylmalonic acid, the condensate of 1-hydroxyethyl-2,2,6,6-tetramethyl-4-hydroxypiperidine and succinic acid, the condensate of ,N'-bis(2,2,6,6-tetramethyl-4-piperidyl)-hexamethylenediamine and 4-tert-octylamino-2,6-dichloro-1,3,5-s-triazine, tris(2,2,6,6-tetramethyl-4-piperidyl)-nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis-(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxy-propoxy)phenyl]-4,6-bis(2,4-dimethylphenyl)-1,3,5-triazine, 2-[2-hydroxy-4-(2-hydroxy-3-octyloxy-propoxy)-phenyl]-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, ,N'-bis(3,5-di-tert-butyl-4-hydroxyphenylpropionyl)hydrazine, 3-salicyloylamino-1,2,4-triazole, bis(benzylidene)oxalic dihydrazide, oxanilide, isophthalic dihydrazide, sebacic bis(phenylhydrazide), N,N'-diacetaladipic dihydrazide, N,N'-bis(salicyloyl)oxalic dihydrazide, N,N'-bis(salicyloyl)thiopropionic dihydrazide.

4. Further phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, bis(2,6-di-tert-butyl-4-methylphenyl)pentaerythritol diphosphite, bis(isodecyloxy)pentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine.

5. Compounds which decompose peroxide, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher &atty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

The invention is illustrated in more detail by the following Examples in which, unless otherwise stated, all parts and percentages are by weight, as also throughout the remainder of the description.

EXAMPLE 1

Decyl*-tetramethylolcyclohexanol bisphosphite (=compound of formula I, wherein $R_1=H$, $m=n=1$, $R_2=$decyl*)

*mixture of isomeric decyl alcohols

A) With stirring, a mixture of 496.5 g of triphenylphosphite, 176.1 g of 2,2,6,6-tetramethylolcyclohexanol and 2.6 g of sodium methylate is heated to 110° C., kept for 3 hours at this temperature, and the phenol formed is then removed by vacuum distillation, giving 98% of theory of phenyltetramethylolcyclohexanol bisphosphite.

B) To this compound are added 126.6 g of decanol and an additional 2.6 g of sodium methylate. The reaction mixture is heated to 110° C. and stirred for another 3 hours at this this temperature. The phenol formed is subsequently removed by vacuum distillation and the product is clarified by filtration after addition of 2 g of filter aid, giving 298,2 g (86% of theory) of the title product as a brown viscous liquid which has a refractive index of
$n_D^{20}=1.5125$.

Elemental analysis: P calcd: 14.26%; found: 14.28%.

$^{31}$P-nuclear resonance spectrum (recorded in deuterochloroform):
$P^\alpha$ 94.4 ppm
$P^\beta$ 123.5 ppm

EXAMPLES 2-6

The compounds of Examples 2-6 are prepared by the same general procedure as described for the compound of Example 1, except that the transesterification is carried out with an alcohol corresponding to the radical A. The compounds of formula I, wherein $m=1$ and $R_1=H$, and their characteristic data are listed in Table 1.

TABLE 1

| Ex. | A | n | Yield [%] | $n_D^{20}$/m.p. [°C.] |
| --- | --- | --- | --- | --- |
| 2 | $C_4H_9-O-C_2H_4-O-C_2H_4-O-$ | 1 | 72 | 1.5105 |
| 3 | $C_4H_9-CH(C_2H_5)-CH_2-O-$ | 1 | 95 | 1.5100 |
| 4 | $C_{13/15}H_{27/31}-O-$ * | 1 | 72 | 1.5000 |
| 5 | $C_9H_{19}-C_6H_4-O-$ | 1 | 49 | 1.5374 |
| 6 | $C_6H_5-O-$ | 1 | 88 | 1.5685 |
| 7 | $n-C_{18}H_{37}-O-$ | 1 | 95 | 47–50 |
| 8 | $n-C_8H_{17}-CH(n-C_8H_{17})-CH_2-O-$ | 1 | 93 | 1.4969 |
| 9 | $n-C_{12}H_{25}-CH(n-C_{10}H_{21})-CH_2-O-$ | 1 | 98 | 1.4925 |
| 10 | $n-C_{10}H_{24}-CH(n-C_8H_{17})-CH_2-O-$ | 1 | 98 | 1.4937 |
| 11 | $n-C_6H_{13}-CH(n-C_4H_9)-CH_2-O-$ | 1 | 92 | 1.5032 |
| 12 | $-O-(CH_2)_{10}-O-$ | 2 | 97 | 1.5348 |
| 13 | $-O-(CH_2CH_2O)_8-$ | 2 | 98 | 1.5219 |
| 14 | $-O-(CH_2CH_2O)_6-$ | 2 | 98 | resin |
| 15 | $C_6H_5-CH_2CH_2CH_2O-$ | 1 | 98 | 1.5481*** |

TABLE 1-continued

| Ex. | A | n | Yield [%] | $n_D^{20}$/m.p. [°C.] |
|---|---|---|---|---|
| 16 | 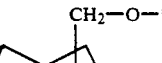 | 2 | 99 | glass 1.5246**** |
| 17 |  | 2 | 97 | resin |
| 18 |  | 4 | 98 | glass 1.5213**** |

*The alcohol used in ACROPOL ® 35, a commercial product sold by EXXON and consisting of a mixture of linear $C_{13/15}$ primary alcohols having more than 56% linearity (Chem. Abstr. No. 67762-41-8*)
**Tricyclodecyldimethanol (TCD-DM alcohol, ex Farbwerke Hoechst), mixture of isomeric tricyclic primary $C_{12}$diols
***The refractive index is measured at 40° C.
****To determine the refractive index, the product is analysed in a 50% solution in toluene.

EXAMPLE 19

186 g of the phenyltetramethylolcyclohexanol bisphosphite intermediate prepared according to Example 1A are transesterified with 222 g of Desmophen ® 550 U in the presence of 0.75 g of sodium methylate under nitrogen at 120°-160° C./2 Pa. The phenol formed is removed by distillation. Yield: 360 g of a pale resin with a viscosity of 4770 mPa.s (25° C.) as product.

$^{31}$P-nuclear resonance spectrum
$P^\alpha$ 95.7 ppm
$P^\beta$ 122.9 ppm

EXAMPLE 20-26

The compounds of Examples 20-26 are prepared in accordance with the general procedure of Example 19 by reacting phenyltetramethylolcyclohexanol bisphosphite with the polyether polyols or polyether/ester polyols listed in Table 2. The polyols used and the physical properties of the products are indicated in Table 2.

TABLE 2

| Ex. | Polyether(ester)polyol | P content [%] | Viscosity mPa s | T[°C.] |
|---|---|---|---|---|
| 20 | Voranol ®-CP 1055 | 4.82 | 3180 | 25 |
| 21 | Desmophen ®-1140 U | 6.33 | 440 | 80 |
| 22 | Desmophen ®-1155 U | 4.45 | 290 | 80 |
| 23 | Voranol ®-CP 455 | 8.26 | 240 | 80 |
| 24 | Voranol ®-CP 755 | 6.12 | 155 | 80 |
| 25 | Lupranol ®-3321 | 8.57 | 5190 | 80 |
| 26 | Lupranol ®-3421 | 9.37 | 5980 | 80 |

Voranol, product sold by DOW Chemical Comp.
Desmophen, product sold by Bayer AG
Lupranol, product sold by BASF

EXAMPLE 27

Mill ageing test
The following basic formulation is used for the test in PVC:
100 parts: of S-PVC ®Corvic S 71/102 (ex ICI)
20 parts: of dioctyl phtalate
2 parts: of stabiliser The stabiliser is a mixture of barium/zinc carboxylates/phenolates containing 11.2% of Ba and 2.2% of Zn and, in addition to 10% of ®SHELL-SOL A (ex SHELL; mixture of aromatic hydrocarbons with an aromatic content of 98%; boiling range 165°-185° C., DIN 51 751) as solvent, contains 24.3% of the phosphite of Example 2 as co-stabiliser.

A mill ageing test is carried out at 190° C. The procedure comprises plastifying the above mixture initially for 5 minutes on a mixer rolls at constant temperature (190° C.). Afterwards 0.33 mm samples are cut from the centre of the sheet at 5 minute intervals. The Yellowness Index (ASTM-D) 1925-70) of these samples is then determined. The results are reported in Table 3.

TABLE 3

| Rolling time [min] | 5 | 10 | 15 | 20 | 25 | 30 | 35 | 40 | 45 | 50 | 55 | 60 |
|---|---|---|---|---|---|---|---|---|---|---|---|---|
| Yellowness Index | 5.7 | 6.4 | 8.0 | 9.7 | 12.4 | 17.1 | 20.8 | 22.0 | 23.3 | 22.9 | 23.3 | 22.5 |

EXAMPLE 28

Mill ageing test
The phosphite of Example 19 is incorporated into the stabiliser system described in Example 27 and subjected to a mill ageing test as in that Example. The results of this test are reported in Table 4.

TABLE 4

| Rolling time | 5 | 10 | 15 | 20 | 25 | 30 | 35 | 40 | 45 | 50 | 55 | 60 |

TABLE 4-continued

| [min] | | | | | | | | | | | |
|---|---|---|---|---|---|---|---|---|---|---|---|
| Yellowness Index | 5.1 | 5.8 | 6.5 | 6.3 | 6.9 | 7.8 | 9.2 | 11.2 | 12.8 | 14.5 | 17.6 | 22.7 |

EXAMPLE 29

Brabender test 100 parts of unstabilised high density polyethylene (®Lupolen 5260 Z; BASF) in powder form are blended dry with 0.1 part of novel bisphosphite and 0.05 part of pentaerythritol tetra[3-(3,5-di-tert-butyl-4-hydroxyphenyl)]propionate and the blend is kneaded for 20 minutes in a Brabender plastograph at 220° C. and 50 rpm. The kneading resistance is determined by the gradient of the torque curve. The increase in torque is an indicator of the onset of crosslinking of the polymer. The time taken until the increase in torque (induction time) is a measure of the efficacy of the processing stabiliser. One minute after the increase in torque, the sample is taken from the Brabender plastograph and pressed at 180° C. to a 2 mm sheet. The Yellow Index of this sheet is then determined. The values obtained are reported in Table 3.

TABLE 5

| Biphosphite of Example | Induction time [min] | Yellowness Index |
|---|---|---|
| 1 | 24.5 | 2.0 |
| 2 | 30.0 | 0.7 |

Long induction times and low Yellowness values denote good stabilisation.

What is claimed is:

1. A compound of formula I

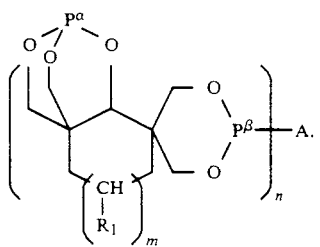

wherein m is 0, 1 or 2, n is 1 to 6, $R_1$ is hydrogen or $C_1$-$C_4$alkyl and, if m=2, the radicals $R_1$ are identical or different, and A is the radical of an at least n-hydric alcohol or phenol, which radical is attached to the P atom or atoms through the alcoholic or phenolic O atom or atoms.

2. A compound according to claim 1, wherein A, if n=1, is —$OR_2$, wherein $R_2$ is $C_1$-$C_{24}$alkyl, unsubstituted or substituted by $C_5$-$C_{12}$cycloalkyl, morpholino, piperidino, piperazino, $C_6$-$C_{16}$alkylcycloalkyl, tetrahydrofuryl, phenyl, phenoxy and/or —$NR_3R_4$; $C_2$-$C_{24}$alkyl which is interrupted by one or more —O—, —S— and/or —$NR_5$ units; unsubstituted or $C_1$-$C_6$alkyl-substituted $C_5$-$C_{12}$cycloalkyl; phenyl, naphthyl or biphenyl, each unsubstituted or substituted by $C_1$-$C_{18}$alkyl, phenyl, phenyl-$C_1$-$C_4$alkyl, cyclopentyl, cyclohexyl and/or $C_2$-$C_4$alkenyl; or unsubstituted or $C_1$-$C_4$alkoxy-substituted phenyl-$C_1$-$C_4$alkyl, $R_3$ and $R_4$ are each independently of the other hydrogen, $C_1$-$C_6$alkyl, phenyl or ($C_1$-$C_4$alkyl)phenyl, $R_5$ is hydrogen, $C_1$-$C_6$alkyl or phenyl, A, if n=2, is a radical —O—Y—O—, wherein Y is $C_2$-$C_{20}$alkylene, $C_2$-$C_{20}$alkenylene or $C_3$-$C_4$alkynylene, each unsubstituted or substituted by $R_6$ and/or $R_7$, $C_2$-$C_{20}$alkylene which is interrupted by O-atoms, $C_5$-$C_6$cycloalkylene, $C_7$-$C_{12}$alkylenecycloalkylene-alkylene, phenylene, naphthylene, 3,4-tetrahydrofurylene,

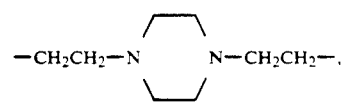

or is a radical —X—B—X—, X is unsubstituted or $C_1$-$C_4$alkyl-substituted $C_1$-$C_{20}$alkylene, $C_5$-$C_6$cycloalkylene, phenylene or phenylene which is substituted by $C_1$-$C_4$alkyl or $C_2$-$C_4$alkenyl, or is a radical

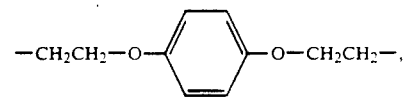

B is a direct bond, —$CR_6R_7$—, —S—, —$SO_2$— or —$NR_5$—, $R_6$ is hydrogen or $C_1$-$C_4$alkyl, $R_7$ is hydrogen, $C_1$-$C_4$alkyl or $C_2$-$C_{12}$alkoxycarbonyl-$C_1$-$C_4$alkyl, or A is

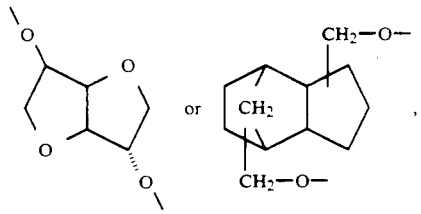

A, if n=3, is

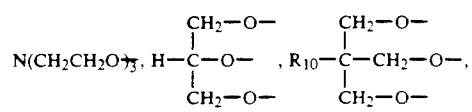

-continued

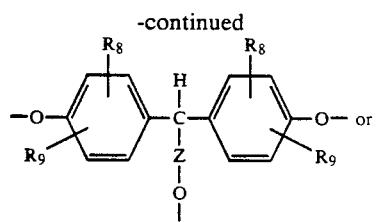

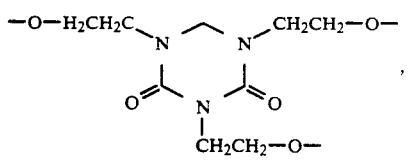

R₈ and R₉ are each independently of the other hydrogen or C₁-C₄alkyl,

R₁₀ is C₁-C₂₄alkyl and

Z is phenylene-(C₁-C₄alkylene) which is substituted by 1 to 4 C₁-C₄alkyl groups, A, if n=4, is

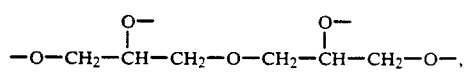

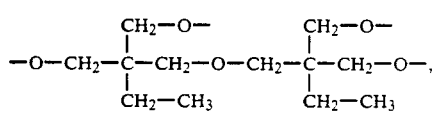

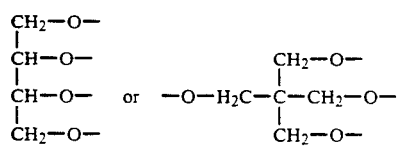

and
A, if n=5 or 6, is

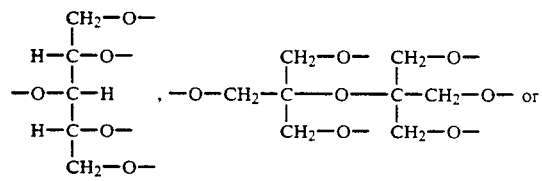

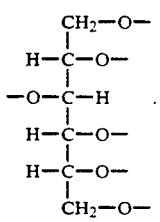

3. A compound according to claim 1, wherein m is 1.

4. A compound according to claim 1, wherein n is 1.

5. A compound according to claim 2, wherein R₂ is unsubstituted or phenyl-substituted C₁-C₂₄alkyl, C₂-C₁₆alkyl which may be interrupted by one or more —O—, —S— or —NH units, unsubstituted or C₁-C₄alkyl-substituted C₅-C₁₀cycloalkyl, unsubstituted phenyl or phenyl which is substituted by C₁-C₁₈alkyl, phenyl or phenyl-C₁-C₄alkyl, naphthyl or phenyl-C₁-C₄alkyl.

6. A compound according to claim 5, wherein R₂ is unsubstituted or phenyl-substituted C₄-C₂₀alkyl, C₄-C₁₂alkyl which may be interrupted by one or more —O—, —S— or —NH units, unsubstituted or C₁-C₄alkyl-substituted C₆-C₁₀cycloalkyl, unsubstituted phenyl or phenyl which is substituted by C₁-C₁₂alkyl, phenyl or phenyl-C₁-C₄alkyl, or R₂ is phenyl-C₁-C₄alkyl.

7. A compound I according to claim 2, wherein if n>1, A is a radical —O—Y—O—, wherein Y is unsubstituted C₂-C₂₀alkylene or C₂-C₂₀alkylene which is substituted by R₆ and/or R₇, C₂-C₂₀alkylene which is interrupted by O atoms, C₇-C₁₂alkylenecycloalkylene-alkylene, phenylene, naphthylene or a radical —X—B—X—, X is unsubstituted or C₁-C₄alkyl-substituted C₁-C₂₀alkylene, phenylene or phenylene which is substituted by C₁-C₄alkyl or C₂-C₄alkenyl, B is a direct bond, —NR₅—, —S— or —CR₆R₇—,
or A is

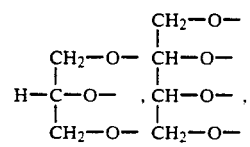

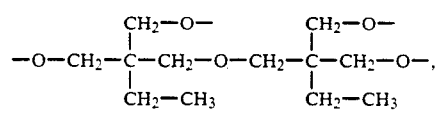

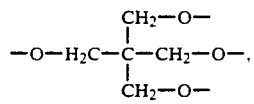

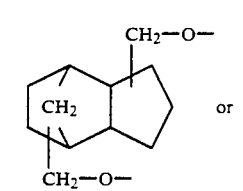

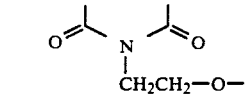

8. A compound according to claim 1, wherein A is the radical of an n-hydric linear or cyclic sugar in which not all OH groups of said sugar are esterified with a biphosphite radical.

9. A compound which is obtainable by reacting a compound of formula II

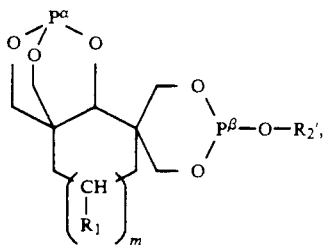
(II)

wherein m is 0, 1 or 2, $R_1$ is hydrogen or $C_1-C_4$alkyl and, if m=2, the radicals $R_1$ are identical or different, and $R_2'$ is phenyl, $C_1-C_{12}$alkylphenyl or $C_1-C_4$alkyl, with a polyether polyol or polyether/ester polyol, the hydroxy functions of said polyether polyol or polyether/ester polyol being partially or completely esterified with the radical

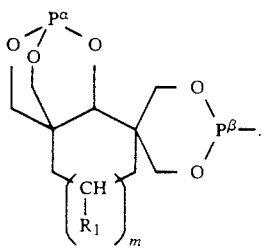

10. A compound according to claim 9, wherein the polyether polyol or polyether/ester polyol is a polyol based on propylene oxide.

11. A composition comprising (a) an organic material which is susceptible to light-induced, thermal and/or oxidative degradation, and (b) at least one compound of formula I as claimed in claim 1.

12. A composition according to claim 11 which contains, in addition to a compound of formula I, customary amounts of further additives.

13. A composition according to claim 12, wherein component (a) is a natural, regenerated or synthetic polymer.

14. A composition according to claim 13, wherein component (a) is a thermoplastic polymer.

15. A composition according to claim 13, wherein component (a) is a polyolefin., preferably a polyvinyl chloride, a polyethylene or polypropylene.

16. A composition according to claim 15, wherein component (a) is a polyvinyl chloride, a polyethylene or polypropylene.

17. A composition according to claim 11, wherein component (a) is a lubricant or a hydraulic fluid.

18. A method for processing thermoplastic polymers, which comprises incorporating into the polymer a compound of formula I as claimed in claim 1.

19. A method for making casting resins or laminates, or binders for the fabrication of honeycomb structures or adhesives, which comprises incorporating a compound as claimed in claim 9.

20. A process for protecting organic material against oxidative, thermal and/or actinic degradation, which comprises incorporating in or applying to said material a compound of formula I as claimed in claim 1 as stabiliser.

* * * * *